US00PP26384P2

(12) United States Plant Patent
Hansen

(10) Patent No.: US PP26,384 P2
(45) Date of Patent: Feb. 2, 2016

(54) ***AGAVE* PLANT NAMED 'DESERT DIAMOND'**

(50) Latin Name: ***Agave hybrida* (Zucc.)**
Varietal Denomination: Desert Diamond

(71) Applicant: Hans A. Hansen, Zeeland, MI (US)

(72) Inventor: Hans A. Hansen, Zeeland, MI (US)

(73) Assignee: Walters Gardens, Inc., Zeeland, MI (US)

( * ) Notice: Subject to any disclaimer, the term of this patent is extended or adjusted under 35 U.S.C. 154(b) by 138 days.

(21) Appl. No.: 13/998,791

(22) Filed: Dec. 6, 2013

(51) Int. Cl.
*A01H 5/00* (2006.01)

(52) U.S. Cl.
USPC ..... Plt./373

(58) Field of Classification Search
USPC ..... Plt./373, 263.1
See application file for complete search history.

*Primary Examiner* — Keith Robinson

(57) ABSTRACT

A new and unique *Agave* plant named 'Desert Diamond' characterized by compact rounded plant habit and variegated leaves with white margins and gray-green centers.

1 Drawing Sheet

Botanical classification: *Agave hybrida* (Zucc.).
Variety denomination: 'Desert Diamond'.

BACKGROUND OF THE INVENTION

The present invention relates to the new and distinct Variegated Butterfly *Agave* plant, *Agave* 'Desert Diamond' discovered by Hans A. Hansen at a nursery in Zeeland, Mich., USA as an uninduced whole-plant mutation in a tissue cultured crop of *Agave potatorum* 'Kissho Kan' (not patented) the summer of 2005. The new plant has been successfully asexually propagated both by division and by tissue culture at a nursery in Zeeland, Mich. Both methods of asexual propagation systems have been found produce stable and identical plants that maintain the unique characteristics of the original plant.

BRIEF SUMMARY OF THE INVENTION

*Agave* 'Desert Diamond' differs from its parent, 'Kissho Kan', as well as all other *Agaves* known to the applicant. The most similar known *Agave* cultivars are: 'Cream Spike' (not patented), 'AGAVWS' U.S. Plant Pat. No. 21,854, and 'Kara's Stripes' U.S. Plant Pat. No. 19,444. *Agave* 'Cream Spike' is of the species *parryi*, while the other two comparison cultivars are of the species *attenuata*. 'Kara's Stripes' has longer leaves with yellow centers and thin green margins and develops into a much taller and broader plant than 'Desert Diamond'. Similarly, 'AGAVWS' has longer leaves and develops into a much taller and broader plant but has variegation of white margins and green centers similar to that of the new plant. *Agave potatorum* 'Snowflake' has similar variegation and pattern, but the foliage is more open and the apex of the foliage is more tapered than the instant plant. In comparison to the sport parent, 'Desert Diamond' has a similar pattern of variegation, but the margins are a much lighter white rather than the creamy-greenish white of 'Kissho Kan'.

*Agave* 'Desert Diamond' differs from all other *Agaves* known to the applicant, by the combination of the following traits:

1. Compact dense plant habit.
2. Short leaves with white margins and gray-green centers.
3. Leave apices abbreviated producing a short leaf.

BRIEF DESCRIPTION OF THE DRAWINGS

The photograph of the new plant demonstrates the overall appearance of the new plant including the unique traits as a two-year old plant grown in a container in a greenhouse with supplemental water and fertilizer as needed. The colors are as accurate as reasonably possible with color reproductions. Ambient light spectrum, temperature, source and direction may cause the appearance of minor variation in color.

The drawing shows the new plant in a container.

DETAILED BOTANICAL DESCRIPTION

The following descriptions and color references are based on the 2001 edition of The Royal Horticultural Society Colour Chart except where common dictionary terms are used. The new plant, *Agave* 'Desert Diamond', has not been observed under all possible environments. The phenotype may vary slightly with different environmental conditions, such as temperature, light, fertility, moisture and maturity levels, but without any change in the genotype. The following observations and size descriptions are of a two-year old plant in a commercial wholesale greenhouse in Zeeland, Mich. with supplemental water and fertilizer as needed.

Botanical classification: *Agave hybrida* (Zucc.).
Variety denomination: 'Desert Diamond'.
Sport parentage: Uninduced whole-plant sport of *Agave* 'Kissho Kan'.
Propagation: Garden division and sterile plant tissue culture.
Time to initiate roots from tissue culture: About 18 days; offsets of 2.5 cm diameter would already have established roots.
Growth rate: Moderate.
Crop time: About 12 weeks to finish during the summer in a 3.8 liter container from an established 2.5 cm tissue culture plug.
Rooting habit: Fleshy, lightly branching, with roots up to 15 cm long.

Root color: Nearest RHS 158C.

Plant shape and habit: Herbaceous perennial with basal rosettes of leaves emerging from central base, producing a symmetrical rounded mound.

Plant size: Foliage height about 11.0 cm tall from soil line to the top of the leaves and about 17.0 cm wide at the widest point just above soil line.

Foliage description: Spatulate, simple, fleshy; margins slightly cupped upward toward apex; acute spinose leaf apex; truncate sessile base; margins serrate and spinose.

Number of leaves: About 32 per plant.

Leaf blades: About 7.5 cm long, 5.0 cm wide and 5.0 mm thick; usually bi-laterally symmetrical; glabrous and glaucous above and below; adaxial variegation with wide margin between about 1.5 cm wide in the blade center tapering toward apex; pattern variable with finger-like projections jetting from darker center into lighter margin; darker center to about 2.5 cm wide; abaxial lighter margin about 8.0 mm wide in leaf center narrowing toward apex; abaxial darker center about 3.5 cm wide with less projections jetting into lighter margin.

Foliage fragrance: None observed.

Leaf blade colon:

*Adaxial* (*top*) *margin*.—Lighter (more white) than RHS 155D.

*Abaxial* (*bottom*) *margin*.—Lighter (more white) than RHS 155D.

*Adaxial center*.—More green than RHS 122C and more blue than RHS 138D.

*Abaxial center*.—More green than RHS 122C and more blue than RHS N138D.

Spines: Lateral spines about 2.5 mm long with curve backward away from leaf apex; apical spine straight, about 1.0 cm long; color of lateral and apical spines nearest RHS N186B.

Spine texture: Stiff, glabrous, sharply pointed.

Petiole: Sessile.

Veins: Absent.

Stem: Short, completely covered with leaves.

Flower description: Flowers have not yet been observed.

Fruit and seed: Have not yet been observed.

Disease resistance: *Agave* 'Desert Diamond' has not been observed to be resistant to diseases common to *Agaves* beyond that which is normal for *Agave*. The plant is xeromorphic and survives well with minimal water once established. Hardiness at least from USDA zone 10. Extent of winter hardiness has not been tested.

I claim:

1. A new and distinct cultivar of ornamental *Agave* plant named 'Desert Diamond' as herein described and illustrated, suitable as a potted plant, for the garden.

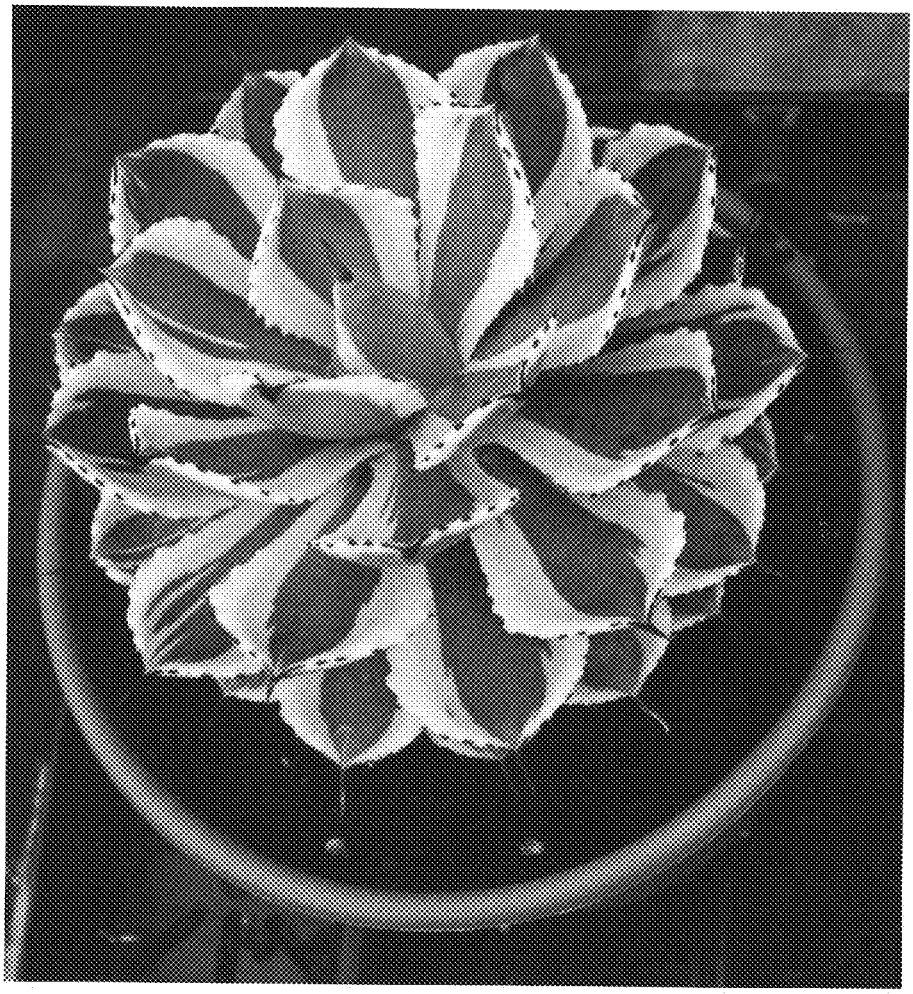

* * * * *